(12) United States Patent
Adams et al.

(10) Patent No.: US 7,887,504 B2
(45) Date of Patent: Feb. 15, 2011

(54) APPARATUS AND METHOD FOR REMOVING MATERIAL FROM THE COLON

(75) Inventors: Mark L. Adams, Sandy, UT (US); Oscar R. Carrillo, Jr., Attleboro, MA (US); Michael S. H. Chu, Brookline, MA (US); Paul DiCarlo, Middleboro, MA (US); Kristian DiMatteo, Waltham, MA (US); Robert F. Rioux, Waltham, MA (US); William J. Shaw, Cambridge, MA (US); Vincent A. Turturro, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 726 days.

(21) Appl. No.: 11/220,519

(22) Filed: Sep. 8, 2005

(65) Prior Publication Data

US 2007/0055139 A1    Mar. 8, 2007

(51) Int. Cl.
*A61B 10/00* (2006.01)
*A61M 3/00* (2006.01)
(52) U.S. Cl. ........................ 604/43; 600/563
(58) Field of Classification Search ............ 600/563, 600/573, 581; 604/27, 30, 39, 43, 317, 327, 604/328
See application file for complete search history.

(56) References Cited

U.S. PATENT DOCUMENTS

| | | | | |
|---|---|---|---|---|
| 1,211,928 A | * | 1/1917 | Fisher | 604/40 |
| 2,148,541 A | * | 2/1939 | Dierker | 604/40 |
| 2,494,088 A | | 1/1950 | Dulity | |
| 3,771,522 A | | 11/1973 | Waysilk et al. | |
| 3,885,567 A | * | 5/1975 | Ross | 604/120 |
| 4,468,216 A | * | 8/1984 | Muto | 604/43 |
| 4,573,965 A | | 3/1986 | Russo | |
| 5,025,778 A | | 6/1991 | Silverstein et al. | |
| 5,178,611 A | | 1/1993 | Rosenberg | |
| 5,269,785 A | | 12/1993 | Bonutti | |
| 5,483,951 A | | 1/1996 | Frassica et al. | |
| 5,512,045 A | * | 4/1996 | Gurchumelidze | 604/31 |

(Continued)

OTHER PUBLICATIONS

Merriam-Webster's Collegiate Dictionary, 10$^{th}$ ed., Merriam-Webster, Incorporated. 2001. p. 207.*

(Continued)

*Primary Examiner*—Max Hindenburg
*Assistant Examiner*—Jonathan M. Foreman
(74) *Attorney, Agent, or Firm*—Finnegan, Henderson, Farabow, Garrett & Dunner, LLP

(57) ABSTRACT

An apparatus includes an elongate body including a proximal end portion and a distal end portion and configured to be at least partially inserted into a body cavity. The elongate body defines a first passageway and a second passageway. The first passageway is configured to communicate fluid from the distal end portion in a first direction, and the second passageway is configured to communicate material from outside of the elongate body into the distal end portion in a second direction opposite the first direction and includes at least one port. An actuator is coupled to the elongate body and is configured to guide the distal end of the elongate body to an area of interest identifiable by a virtual colonoscopy.

19 Claims, 11 Drawing Sheets

U.S. PATENT DOCUMENTS

| | | | |
|---|---|---|---|
| 5,931,833 A | 8/1999 | Silverstein | |
| 5,947,988 A * | 9/1999 | Smith | 606/167 |
| 6,468,203 B2 | 10/2002 | Belson | |
| 6,610,007 B2 | 8/2003 | Belson et al. | |
| 6,902,559 B2 * | 6/2005 | Taufig | 604/542 |
| 7,322,953 B2 * | 1/2008 | Redinger | 604/43 |
| 2001/0025134 A1 * | 9/2001 | Bon et al. | 600/146 |

OTHER PUBLICATIONS

Complementary & Alternative Medicine, Aetna InteliHealth, Dec. 15, 2004, http://www.intelihealth.com/IH/ihtIH/WSIHW000/8513/34968/358752.html?d=dmtCont..., 4 pages.

U.S. Appl. No. 60/614,929.

* cited by examiner

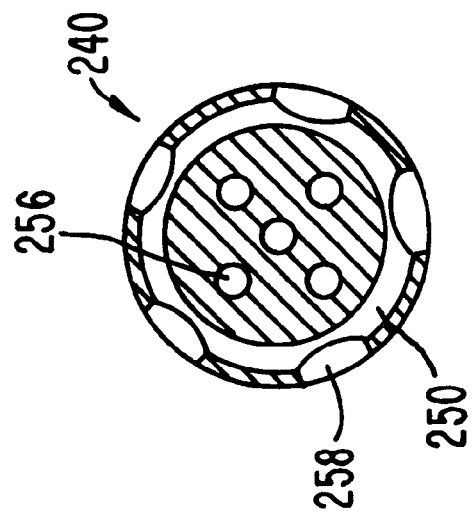
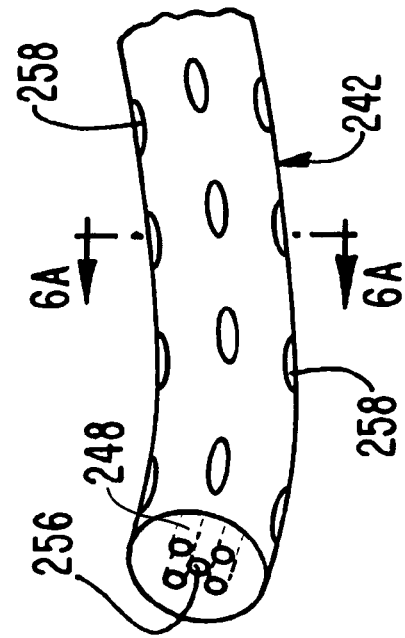
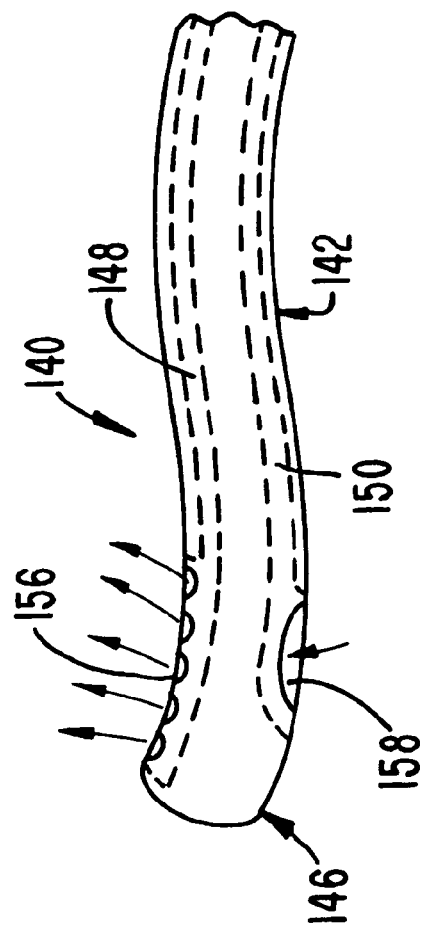

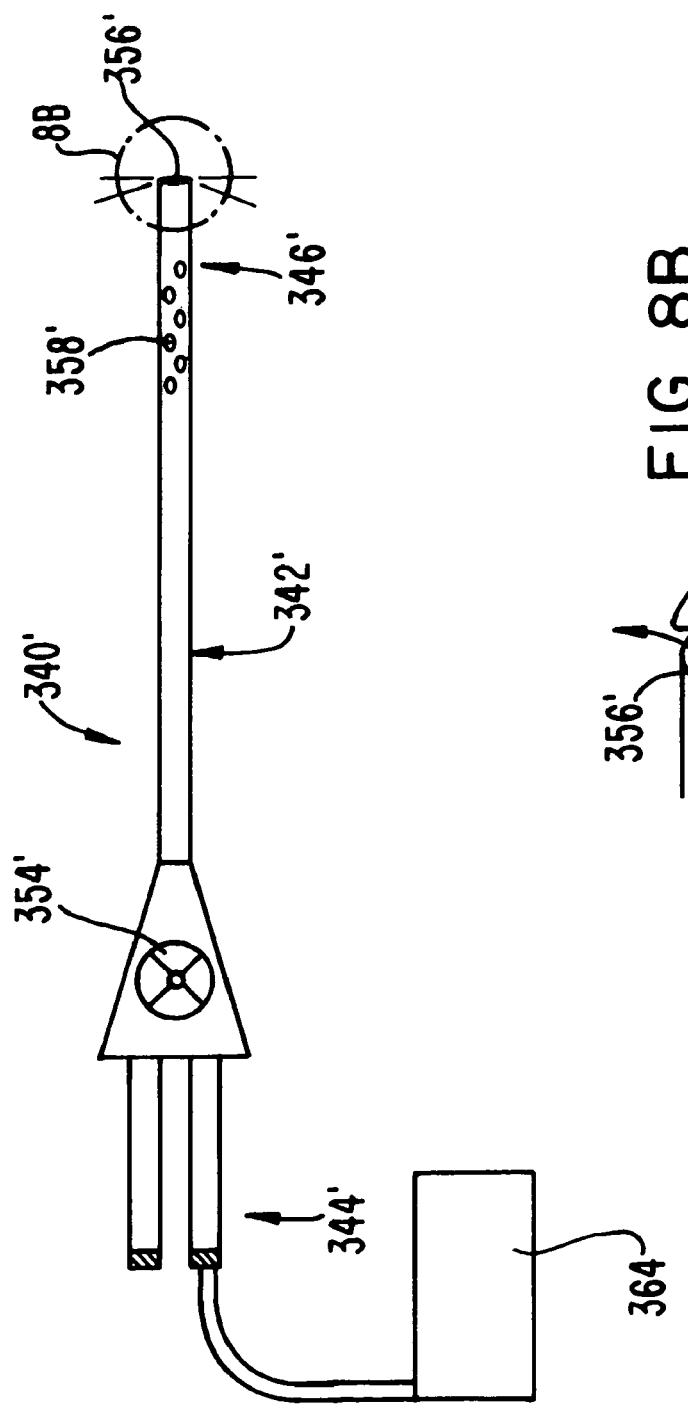
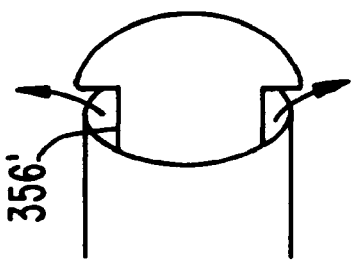

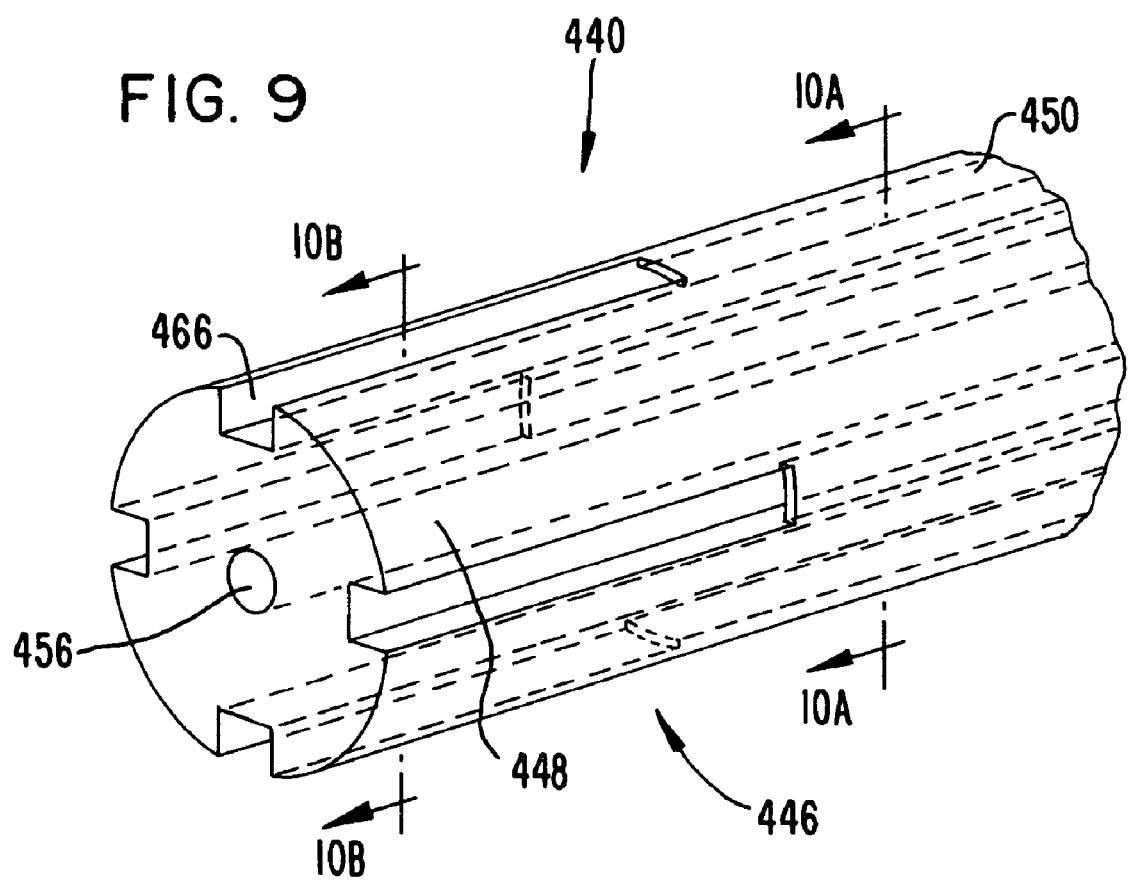

APPARATUS AND METHOD FOR REMOVING MATERIAL FROM THE COLON

BACKGROUND

The present invention relates generally to medical devices for use in conjunction with a virtual colonoscopy procedure, and more particularly to an apparatus and method for removing material from a colon in conjunction with a virtual colonoscopy procedure.

Colorectal cancer is one of the leading causes of deaths from malignancy in the United States, with only lung cancer causing more deaths annually. Colon cancer can be prevented because it usually begins as a benign polyp that grows slowly for several years before becoming cancerous. If polyps are detected and removed, the risk of developing colon cancer is significantly reduced.

Unfortunately, widespread colorectal screening and preventive efforts are hampered by several practical impediments, including limited resources, methodologic inadequacies, and poor patient acceptance leading to poor compliance. Moreover, some tests, such as the fecal occult blood test (FOBT) fail to detect the majority of cancers and pre-cancerous polyps. Additionally, since a sigmoidoscopy only examines a portion of the colon, it also misses many polyps that occur in the remainder of the colon. The accuracy of other tests, such as the barium enema, vary and are not always reliable.

A technique for detecting colorectal cancer using helical computed tomography (CT) to create computer simulated intraluminal flights through the colon was proposed as a novel approach for detecting colorectal neoplasms by Vining D J, Shifrin R Y, Grishaw E K, Liu K, Gelfand D W, *Virtual colonoscopy* (Abst), Radiology Scientific Prgm 1994; 193 (P):446. This technique was first described by Vining et al. in an earlier abstract by Vining D J, Gelfand D W, Noninvasive colonoscopy using helical CT scanning, 3D reconstruction, and virtual reality (Abst), SGR Scientific Program, 1994. This technique, referred to as "virtual colonoscopy", requires a cleansed colon insufflated with air, a helical CT scan of approximately 30 seconds, and specialized three-dimensional (3D) imaging software to extract and display the mucosal surface. The resulting endoluminal images generated by the CT scan are displayed to a medical practitioner for diagnostic purposes.

There have been several advances in virtual colonoscopy that have improved the imaging techniques, making it a more viable and effective screening option. One advantage of using a virtual colonoscopy as a screening process is the elimination of the invasiveness of a traditional colonoscopy. Traditional colonoscopies are preformed using a colonoscope that has a relatively large diameter (i.e., sufficient to form a seal with the anus) that includes, among other instruments, a scope, multiple lumens for introducing gas and/or liquid, and a working channel for introducing a snare or similar device into the colon. With such a device, there is a risk of straightening and/or perforating the colon because of its relative inflexibility and size.

Another advantage of the virtual colonoscopy procedure is the elimination of the preparation process associated with a traditional colonoscopy. The typical preparation process involves the use of strong laxatives to purge any fecal waste from the colon. Such a process is extremely uncomfortable and is often cited as one of the least desirable parts of the whole procedure. Complete purging is not necessary with the virtual colonoscopy procedure. Rather, a fecal contrasting agent is used to facilitate digital subtraction of any residual feces from the virtual image.

In a virtual colonoscopy procedure, if an area is identified that requires closer inspection, the colon may have to be at least partially purged. In the event some residual material is left in the colon, it is desirable to remove that material using devices that have a smaller diameter than existing colonoscopic devices.

During the virtual colonoscopy procedure, the patient lies on the CT scan area. A thin tube (approximately the diameter of a rectal thermometer) is placed in the rectum, through which air is introduced into in the colon. The air is necessary to distend the bowel allowing any polyps to stand out from the normal surface. The patient holds their breath while the machine sweeps over the abdomen. The procedure is repeated with the patient lying on their stomach. The whole procedure takes approximately ten minutes.

In addition to CT scan imaging modalities, magnetic resonance imaging (MRI) can also be used to perform the virtual colonoscopy. When using MRI, only certain tools can be utilized (i.e., tools with only slight ferromagnetic properties).

Even though the virtual colonoscopy is largely non-invasive as a screening process, a need still exists for non-invasive and minimally invasive devices and methods for treating the colon (e.g., removing polyps) in the event the virtual colonoscopy identifies a problem area within the colon.

Some colonoscopy procedures involve insufflating the colon and removing residual material, such as fecal matter, from the colon. When a virtual colonoscopy is performed, the residual material can be identified to help make the extraction procedure easier. As stated above, in a typical colonoscopy, these procedures typically are performed using multiple instruments, such as a colonoscope having an insufflation tool and a working tool. Since the residual material is identified with the virtual colonoscopy, the number of required instruments is reduced; however, there is still a need for further reductions and improvements in instrumentation. Thus, there is a need for a device that provides an improved process for the removal of material from the colon during a colonoscopy procedure being performed in conjunction with a virtual colonoscopy.

SUMMARY OF THE INVENTION

An apparatus includes an elongate body including a proximal end portion and a distal end portion and is configured to be at least partially inserted into a body cavity. The elongate body defines a first passageway and a second passageway. The first passageway is configured to communicate fluid from the distal end portion in a first direction. The second passageway is configured to communicate material from outside of the elongate body into the distal end portion in a second direction opposite the first direction. The second passageway includes at least one port. An actuator is coupled to the elongate body and is configured to guide the distal end of the elongate body to an area of interest identifiable by a virtual colonoscopy.

BRIEF DESCRIPTION OF THE DRAWINGS

The invention is described with reference to the accompanying drawings. In the drawings, like reference numbers indicate identical or functionally similar elements.

FIG. 5 is a side perspective view of a portion of an apparatus according to an embodiment of the invention.

FIG. 6 is a side perspective view of a portion of an apparatus according to another embodiment of the invention.

FIG. 6A is a cross-sectional view taken along line 6A-6A in FIG. 6.

FIG. 8A is a plan view of an apparatus according to an embodiment of the invention.

FIG. 8B is a detailed view of the articulating tip of the apparatus shown in FIG. 8A.

FIG. 9 is a side perspective view of a portion of an apparatus according to an embodiment of the invention.

DETAILED DESCRIPTION

An apparatus includes an elongate body including a proximal end portion and a distal end portion and is configured to be at least partially inserted into a body cavity. The elongate body defines a first passageway and a second passageway. The first passageway is configured to communicate fluid from the distal end portion in a first direction. The second passageway is configured to communicate material from outside of the elongate body into the distal end portion in a second direction opposite the first direction. The second passageway includes at least one port. An actuator is coupled to the elongate body and is configured to guide the distal end of the elongate body to an area of interest identifiable by a virtual colonoscopy.

Figure 1:
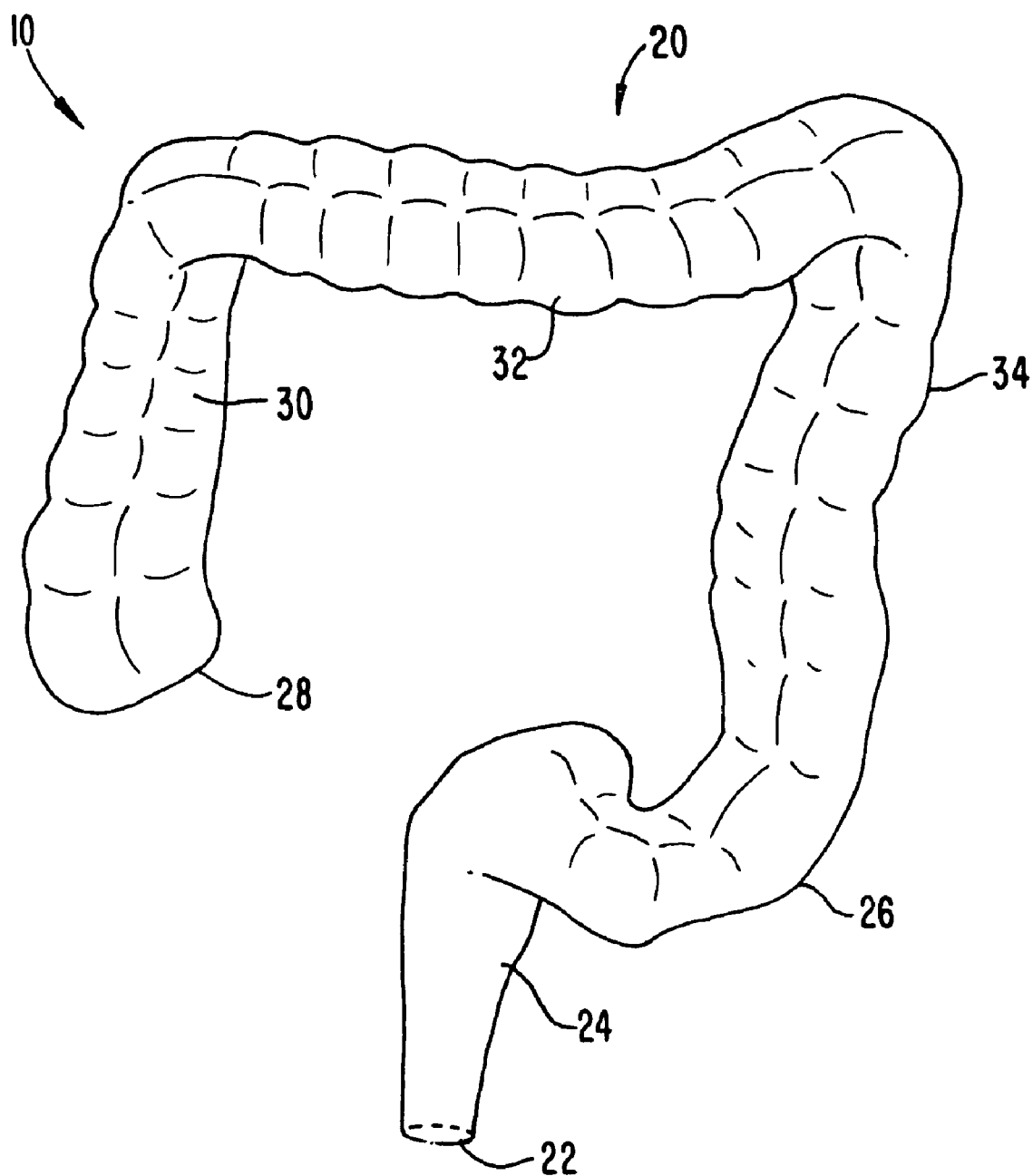
FIG. 1 is an illustration of a large intestine.
Figure 2:
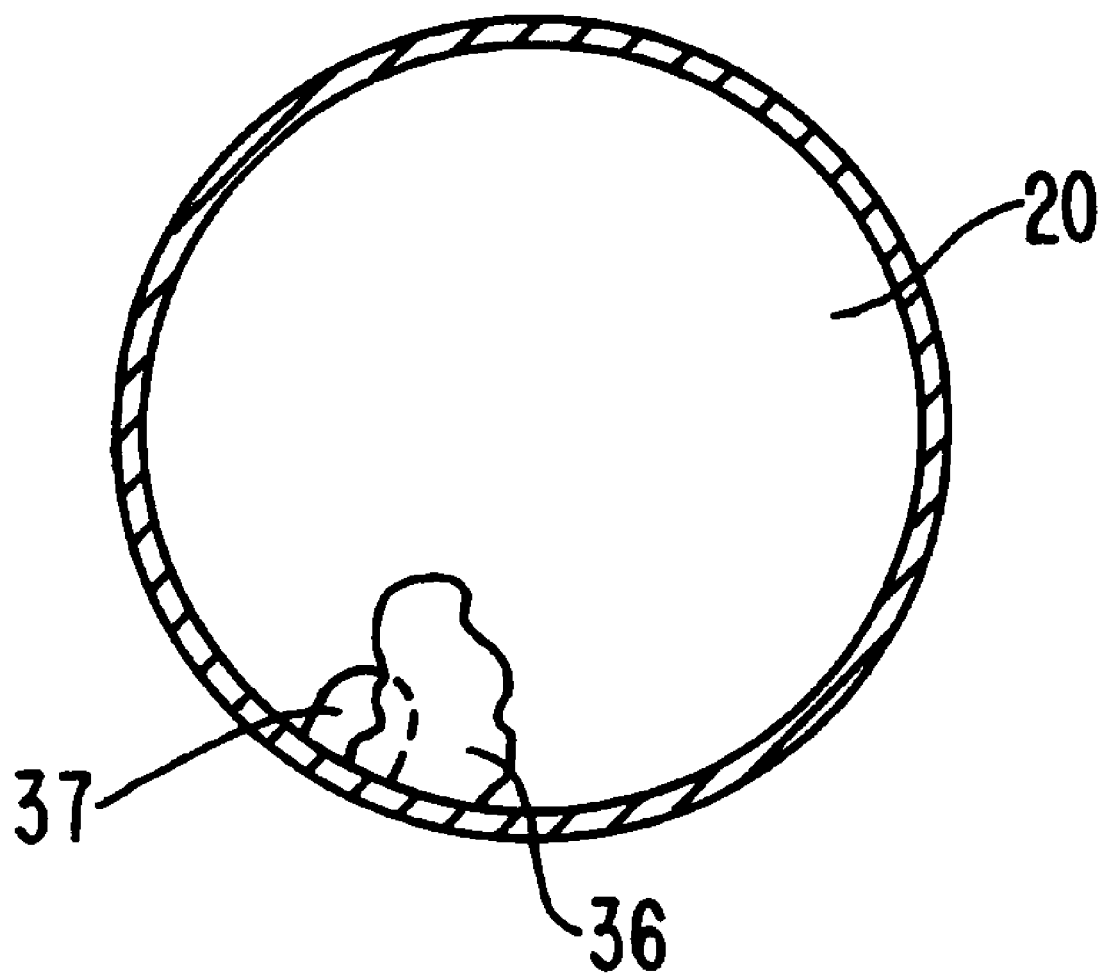
FIG. 2 illustrates residual material located in a colon.

Referring to FIG. 1, an illustration of a large intestine (also called the large bowel) 10 is provided by way of background and reference. The colon 20 is the longest part of the large intestine 10, which is a tube-like organ connected to the small intestine (not illustrated) at one end and the anus 22 at the other. The colon 20 and the rectum 24 form the large intestine 10. The colon 20 is the first 4 to 5 feet of the large intestine 10, and the rectum 24 is the last 4 to 5 inches. The part of the colon 20 that joins to the rectum 24 is called the sigmoid colon 26. The junction of the two parts is often referred to as the rectosigmoid colon or rectosigmoid process. The part of the colon 20 that joins to the small intestine is called the cecum 28. The cecum 28 is adjacent the ascending colon 30, which is connected to the transverse colon 32. The transverse colon 32 is connected to the descending colon 34, which is connected to the sigmoid colon 26. The colon 20 removes/absorbs water and some nutrients and electrolytes from partially digested food. The remaining material, solid waste, called stool or feces, moves through the colon 20 to the rectum 24 and leaves the body through the anus 22. In some cases, feces may become lodged within the colon, requiring removal through a colonoscopy procedure. FIG. 2 illustrates material 36, such as fecal matter, lodged within the colon 20, which may be at least partially covering an area of interest identified in a virtual colonoscopy, such as a polyp 37.

Figure 3:
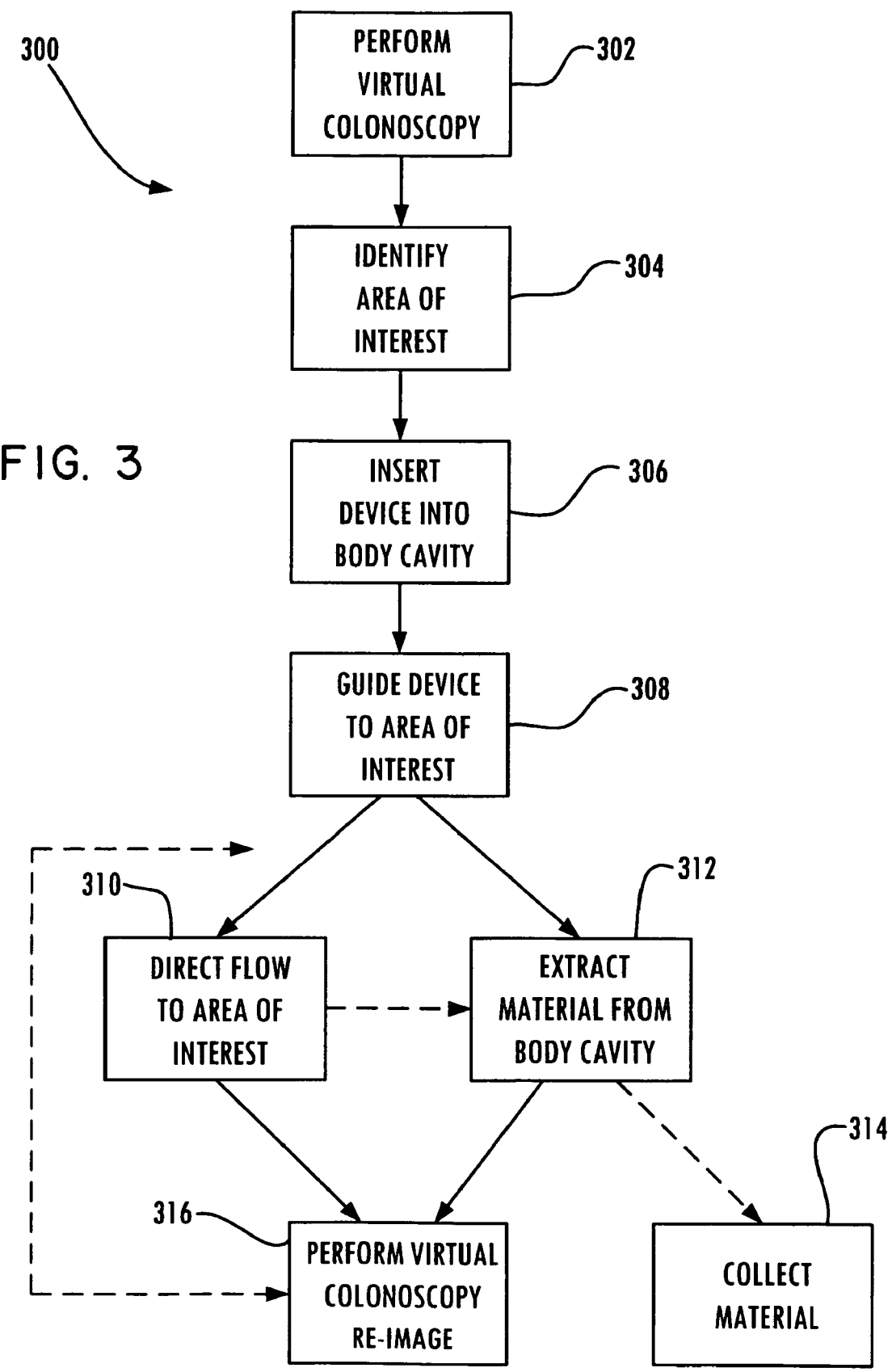
FIG. 3 is a flowchart illustrating a method of using an apparatus according to an embodiment of the invention.

FIG. 3 illustrates a flowchart of a method 300 of using an apparatus according to an embodiment of the invention. In a first step 302, a virtual colonoscopy is performed on a patient using one of the modalities discussed above. Through the virtual imaging provided by the virtual colonoscopy, an area of interest (e.g., a polyp) is identified in step 304. Once the area of interest is identified it can be determined that material (e.g., fecal matter) is lodged within the colon and/or is at least obstructing the area of interest. An apparatus according to an embodiment of the invention is then inserted at least partially into the body cavity of the patient (i.e., the colon) in step 306. In step 308, the apparatus is guided to the area of interest. Once at the area of interest, the apparatus directs fluid, such as water or a chemical solution, towards the area of interest to at least partially dilute (or dissolve) the material in step 310. The apparatus then extracts the at least partially diluted material from the colon in step 312. The at least partially diluted material can be collected in a container for further evaluation in step 314. In some embodiments, the fluid is directed towards the area of interest and the at least partially diluted material is removed simultaneously (i.e., steps 310 and 312 are simultaneous). In other embodiments, the fluid can be directed towards the area of interest and the at least partially diluted material can be extracted sequentially (i.e., steps 310 and 312 occur sequentially). In one embodiment, the fluid is directed towards the area of interest intermittently. In some embodiments, re-imaging can be performed to determine the location of the apparatus and/or confirm removal of the material in step 316. Further, in some embodiments, if the re-imaging step reveals that the material has not been sufficiently removed, steps 310, 312 and 316 can be repeated one or more times until the material is sufficiently removed.

Figure 4:
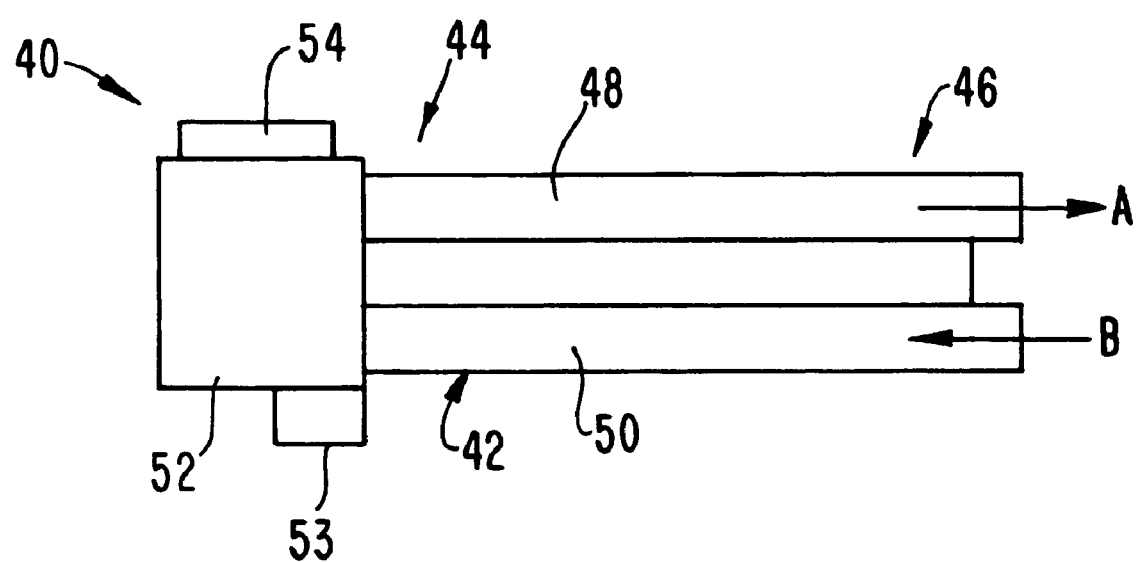
FIG. 4 is a schematic illustration of an apparatus according to an embodiment of the invention.

FIG. 4 is a schematic illustration of an apparatus 40 according to an embodiment of the invention. An apparatus 40 includes an elongate body 42 having a proximal end portion 44 and a distal end portion 46 and is configured to be inserted at least partially into a body cavity of a patient (e.g., through the anus 22 and into the colon 20). The elongate body 42 defines a first passageway 48 and a second passageway 50, each extending between the proximal end portion 44 and the distal end portion 46. Apparatus 40 may also include a controller 52 coupled to elongate body 42 and an actuator 54 coupled to elongate body 42.

First passageway 48 is configured to communicate a fluid, such as water or a chemical solution, in a first direction indicated by arrow A through elongate body 42 and into a body cavity of the patient. Second passageway 50 is configured to communicate material, such as fecal matter diluted with fluid, from within the body cavity into the distal end portion and through elongate body 42 in a second direction opposite the first direction, indicated by arrow B. The fluid being communicated from first passageway 48 can be directed toward an area of interest in the body cavity identified during a virtual colonoscopy procedure. For example, an area of interest may be identified where material is lodged adjacent to, and/or overlying, the area of interest in the body cavity. The fluid at least partially dilutes or dissolves the lodged material to allow it to be more easily extracted from the body cavity. The fluid can be communicated through first passageway 48 simultaneously with the extraction of the diluted material. Alternatively, the fluid communication and the extraction of the diluted material can occur sequentially. The fluid may be communicated continuously or intermittently.

The controller 52 is configured to provide the fluid to first passageway 48. The controller 52 is also configured to provide extraction of the diluted material from the body cavity, such as via a suctioning force. The apparatus 40 may also include a pressure limiting device 53 coupled to controller 52. The pressure limiting device 53 can be configured to limit the pressure of the fluid being introduced into the colon. For example, the pressure of the fluid introduced into the colon may be limited to a maximum of 14 psi.

The actuator 54 is configured to guide the distal end portion 46 of elongate body 42 through the colon 20 and to the area of interest. The actuator 54 can be configured to provide both an up/down directional control and/or right/left directional control (such as by deflecting distal end portion 46 with respect to the remainder of apparatus 40). In some embodiments, the apparatus does not include an actuator.

FIG. 5 illustrates one possible implementation of the apparatus of FIG. 4 (in this embodiment, apparatus 140). Only the distal portion of apparatus 140 is shown. Apparatus 140 includes an elongate body 142 including a distal end portion 146 and a proximal end portion 144 (not shown) and is configured to be at least partially inserted into a body cavity of a patient. Although not shown, apparatus 140 can also include an actuator 154 and a controller 152 as discussed above. Elongate body 142 includes a first internal passageway 148 and a second internal passageway 150, each extending between the proximal end portion 144 and the distal end portion 146. First internal passageway 148 and second internal passageway 150 are configured to provide the same functions as described above for apparatus 40. First internal passageway 148 includes one or more output ports 156 and second internal passageway 150 includes one or more input ports 158 (one illustrated in FIG. 5). Output ports 156 communicate the fluid flowing through first passageway 148 to the body cavity of the patient. Input ports 158 receive the diluted material from within the body cavity and communicate the diluted material through second internal passageway 150.

FIGS. 6 and 6A illustrate a portion of an apparatus according to another embodiment of the invention. Apparatus 240 is similar to apparatus 40 and 140 and provides the same diluting and material extraction functions as apparatus 40 and 140. Apparatus 240 includes a plurality of first passageways 248 extending through elongate body 242 and a circumferential second passageway 250 extending through elongate body 242. The plurality of first passageways 248 include a plurality of output ports 256 and are configured to communicate a fluid through elongate body 242 and into the body cavity (not illustrated). The circumferential second passageway 250 includes a plurality of input ports 258 and is configured to communicate the diluted material from within the body cavity through elongate body 242.

Figure 7:
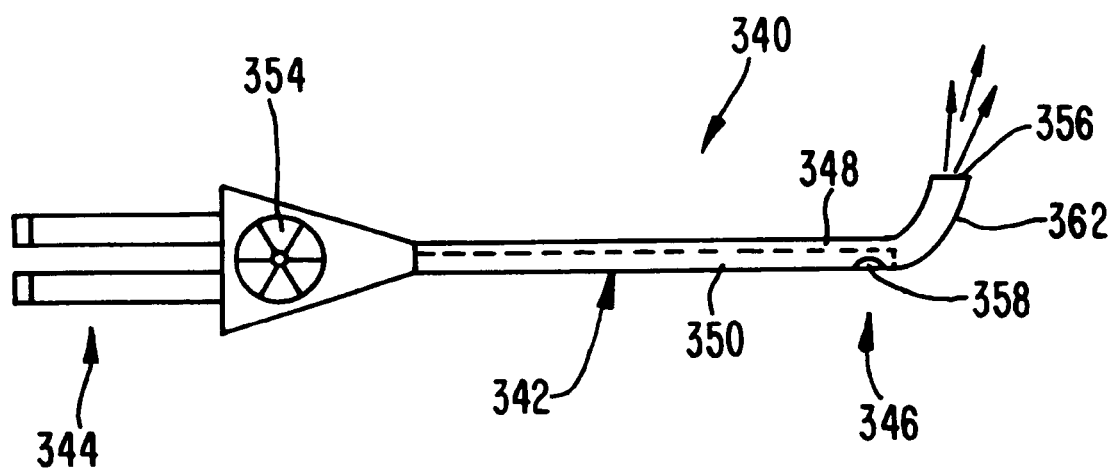
FIG. 7 is a plan view of a portion of an apparatus according to a further embodiment of the invention.

FIG. 7 illustrates an apparatus according to another embodiment of the invention. Apparatus 340 includes an elongate body 342 including a proximal end portion 344 and a distal end portion 346 and is configured to be at least partially inserted into a body cavity of a patient. Apparatus 340 also includes a controller 352 (not shown) and an actuator 354, each coupled to elongate body 342. Elongate body 342 includes a first passageway 348 and a second passageway 350, each extending between the proximal end portion 344 and the distal end portion 346. First passageway 348 and second passageway 350 are configured to provide the same diluting and material extracting functions as described in the previous embodiments. In this embodiment, first passageway 348 includes one output port 356 and second passageway 350 includes at least one input port 358. Output port 356 is configured to communicate the fluid in first passageway 348 to the body cavity (not shown) of the patient. Elongate body 342 is configured with an articulating (e.g., laterally deflectable) tip 362 controlled by actuator 354, to allow for a more focused or directed spray of the fluid towards the area of interest within the body cavity. Input port 358 is configured to receive the diluted material from within the body cavity and communicate the diluted material through second passageway 350.

FIGS. 8A and 8B illustrate another embodiment of an apparatus of the invention. Apparatus 340' is similar to apparatus 340 except apparatus 340' includes a plurality of input ports 358' and an output port 356'. Output port 356' is configured to provide a multi-directional spray of fluid (e.g., 360°) into the body cavity (not shown) of the patient. Apparatus 340' also includes a container 364 coupled to second passageway (not shown in FIG. 8A). Container 364 is configured to collect the extracted diluted material for further evaluation. For example, removed cells may be evaluated for cancer, DNA, nucleic structure, general structure changes, blood content, proteins, fatty acids, and/or antihemoglobin antibodies. Fecal matter may be evaluated for chemicals, age, digestion, occult blood, etc. Other evaluations may include a routine cytologic evaluation, Hemoccult and/or HemoQuant tests.

Figure 10A:
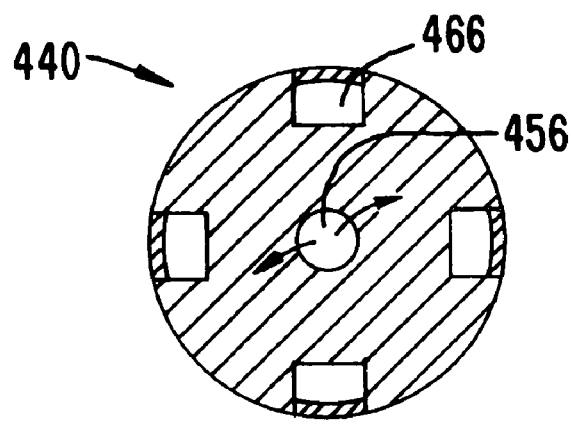
FIG. 10A is a cross-sectional view taken along line 10A-10A in FIG. 9.
Figure 10B:
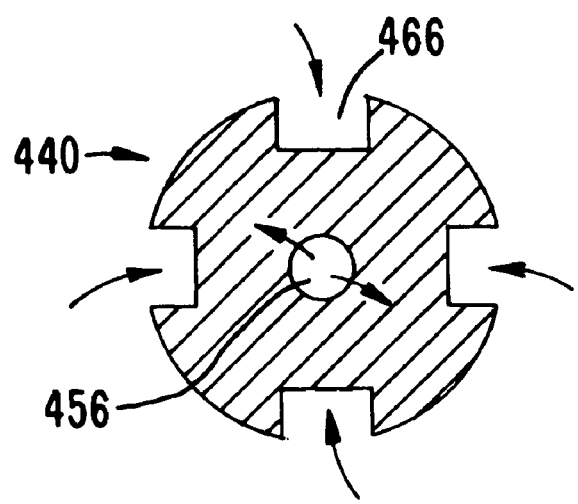
FIG. 10B is a cross-sectional view taken along line 10B-10B in FIG. 9.

FIGS. 9, 10A and 10B illustrate a portion of another embodiment of an apparatus of the invention. Apparatus 440 is configured to provide the same diluting and material extracting functions as the previously described embodiments, except apparatus 440 includes an elongate body defining a first passageway 448 in communication with an opening 456 defined in a distal-most end of the elongate body and a plurality of second passageways 450 having a cut-out side section 466 on distal end portion 446. The cut-out side sections 466 are configured to receive the diluted material being extracted and communicate the material through the plurality of second passageways 450. As shown in FIGS. 9-10B, the cut-out sections 466 have a portion defined by a side wall of the elongate body and a portion defined by the distal-most end of the elongate body.

Figure 11:
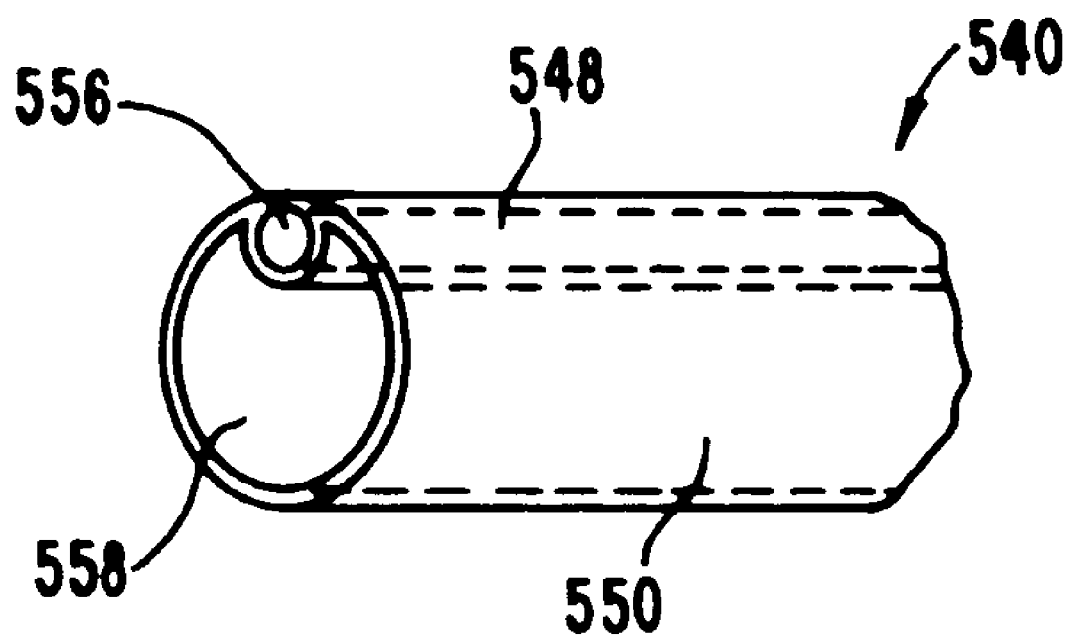
FIG. 11 is a side perspective view of a portion of an apparatus according to an embodiment of the invention.

FIG. 11 illustrates another embodiment of an apparatus of the invention. Apparatus 540 can be configured with all of the same features as the previous embodiments and is configured to perform the same diluting and material extracting functions as the previous described embodiments. Apparatus 540 includes a first passageway 548 including at least one output port 556 to communicate fluid to the body cavity (not shown) of the patient, and a second passageway 550 including at least one input port 558 configured to receive the diluted material being extracted.

Figure 12:
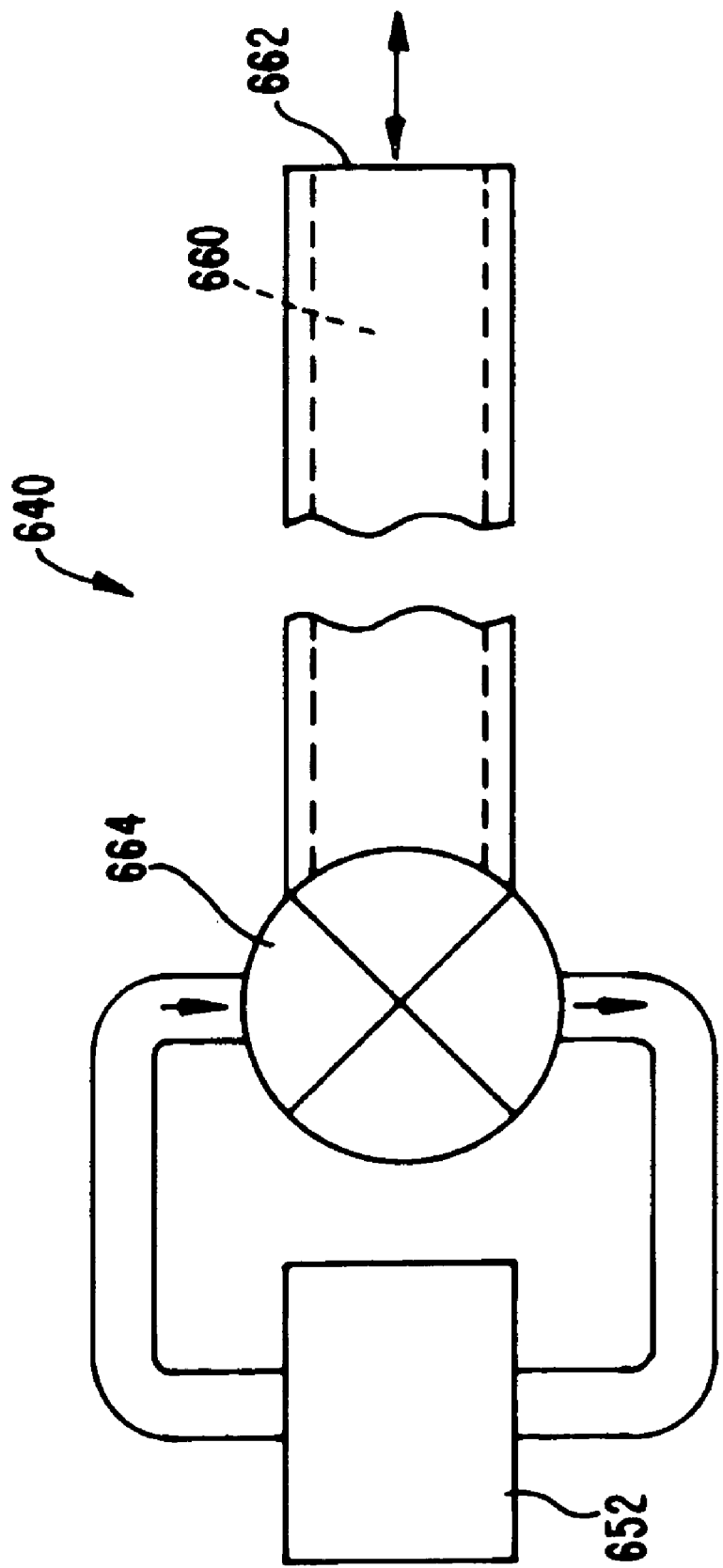
FIG. 12 is a plan view of an apparatus according to an embodiment of the invention.

FIG. 12 illustrates another embodiment of an apparatus of the invention. Apparatus 640 is configured to perform the same diluting and material extracting functions as the previously described embodiments. Apparatus 640 includes a single passageway 660 including a single port 662 to both communicate fluid to the body cavity (not shown) of the patient and to receive the diluted material being extracted. In this embodiment, a valve 664 is coupled to passageway 660. Valve 664 is also coupled to a controller 652. Controller 652 is configured to provide the fluid to passageway 660 and to provide extraction of the diluted material from the body cavity, such as via a suctioning force. Valve 664 is configured to be switched between a fluid communication mode and a material extraction mode to allow both functions to be performed through the same passageway 660.

Apparatus 40 (140, 240, 340, 340', 440, 540, 640) can be constructed with any suitable material(s) conventionally used with medical devices, e.g., metals (stainless steel, titanium), polymers (polyurethane, silicones, polyether, nylon, Teflon), etc. Apparatus 40 (140, 240, 340, 340', 440, 540, 640) is preferably constructed of materials that are suitable for use with the imaging modality selected for the virtual colonoscopy and subsequent confirmatory imaging (e.g., not strongly ferromagnetic for MRI). The apparatus is preferably viewable by the imaging modality (e.g., radiopaque for fluoroscopy, mildly ferromagnetic for MRI).

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention.

For example, although primarily described as including only a single output passageway, an apparatus according to any of the embodiments of the invention can include more than one passageway to communicate fluid to the body cavity. Likewise, any of the embodiments of the invention can include one or more passageways to extract the diluted or dissolved material from the body cavity. In addition, any number of input and output ports can be used. Although described separately with respect to the various embodiments above, some of the features of the disclosed embodiments may be interchangeably associated. For example, although only specifically described with respect to one embodiment, any of the disclosed embodiments can include a container and/or an actuator.

Although the embodiments discussed above were described as using fluid to dissolve or dilute the residual material in the body cavity, in some embodiments, pressurized gas can be used to break up the material.

Although no specific dimensions of the apparatus were associated with the described embodiments, the diameter of the apparatus can be approximately 1-3 mm and the length can be approximately 200-250 cm.

Thus, the various features of apparatus 40 (140, 240, 340, 340', 440, 540, 640) may include other configurations, shapes, sizes not specifically illustrated, while still remaining within the scope of the invention.

What is claimed is:

1. An apparatus, comprising:
    an elongate body including a proximal end portion and a distal end portion, said elongate body configured to be at least partially inserted into a body cavity, said elongate body defining a first passageway and a plurality of second passageways, each of said plurality of second passageways in fluid communication with one of a plurality of elongate cut-out sections, each of said elongate cut-out sections having a length greater than a width defined in part by a side-wall of said elongate body, each of said elongate cut-out sections extending in a direction parallel to a centerline of the elongate body and being disposed circumferentially around said first passageway, wherein each of said plurality of elongate cut-out sections is equally spaced from the centerline of said first passageway at a distal-most end of the first passageway, and having a cross-section that extends through a distal-most end of said elongate body, said first passageway configured to communicate fluid from said distal end portion in a first direction, said plurality of second passageways configured to communicate material from outside of said plurality of elongate cut-out sections of said elongate body into said distal end portion in a second direction opposite the first direction, the first passageway having a length extending from a proximal-most end to a distal-most end of the first passageway, wherein the first passageway is fluidly isolated from each of said plurality of second passageways along said length of said first passageway; and
    an actuator coupled to said elongate body, said actuator configured to guide said distal end portion of said elongate body to an area of interest pre-identified by a virtual colonoscopy.

2. The apparatus of claim 1, further comprising a container coupled to at least one of said plurality of second passageways configured to receive the material communicated through the at least one of said second passageways.

3. The apparatus of claim 1, wherein each one of said plurality of second passageways includes a respective one of a plurality of ports.

4. The apparatus of claim 1, wherein said first passageway includes a plurality of ports.

5. The apparatus of claim 1, further including a controller coupled to said elongate body, said controller provides a suction force to said plurality of second passageways.

6. The apparatus of claim 5, wherein said controller provides said fluid to said first passageway.

7. The apparatus of claim 1, wherein said body cavity is a colon.

8. The apparatus of claim 1, wherein said first passageway is configured to communicate said fluid from said distal end portion intermittently.

9. The apparatus of claim 1, wherein said first passageway is configured to communicate said fluid, and said plurality of second passageways is configured to communicate said material from outside of said elongate body into said distal end portion, simultaneously.

10. The apparatus of claim 1, wherein said first passageway is configured to communicate said fluid, and said plurality of second passageways is configured to communicate said material from outside of said elongate body into said distal end portion, sequentially.

11. The apparatus of claim 1, wherein said plurality of second passageways includes at least three second passageways.

12. An apparatus, comprising:
    an elongate body including a proximal end portion and a distal end portion, said elongate body configured to be at least partially inserted into a body cavity, said elongate body defining a plurality of first passageways and a circumferential second passageway, the circumferential second passageway disposed about and surrounding an entire circumference of a portion of the plurality of first passageways, a distal portion of each of the plurality of first passageways being located in a permanently fixed position relative to a distal portion of the circumferential second passageway throughout operation of the apparatus, each of the plurality of first passageways having a centerline parallel to a centerline of the elongate body along an entire length of each of the plurality of first passageways from a proximal end to a distal end of each of the plurality of first passageways;
    a controller coupled to said elongate body, said controller configured to provide suction to said second passageway; and a container coupled to said elongate body, said plurality of first passageways configured to communicate fluid into said body cavity, said circumferential second passageway configured to communicate material from within said body cavity into said container.

13. The apparatus of claim 12, wherein said controller is configured to provide said fluid to said plurality of first passageways.

14. The apparatus of claim 12, wherein said circumferential second passageway is in fluid communication with a plurality of ports defined by said elongate body, each port from said plurality of ports configured to receive said material from said body cavity therethrough.

15. The apparatus of claim 12, wherein each of said plurality of first passageways is in fluid communication with one of a plurality of ports defined by said elongate body, each port from said plurality of ports configured to communicate said fluid from a respective one of said plurality of first passageways and into said body cavity.

16. The apparatus of claim 12, wherein said body cavity is a colon.

17. The apparatus of claim 12, wherein at least a portion of said elongate body is radiopaque.

18. The apparatus of claim 12, wherein said plurality of first passageways is configured to communicate said fluid into said body cavity intermittently.

19. The apparatus of claim 12, wherein said plurality of first passageways is configured to communicate said fluid into said body cavity, and said circumferential second passageway is configured to communicate said material from said body cavity and into said container, simultaneously.

* * * * *